(12) United States Patent
Oh et al.

(10) Patent No.: US 10,285,713 B2
(45) Date of Patent: May 14, 2019

(54) GUIDE DEVICE FOR KNEE REPLACEMENT

(71) Applicant: CORENTEC CO., LTD, Chungcheongnam-do (KR)

(72) Inventors: Seung-Hun Oh, Seoul (KR); Seok-Ju Kim, Seoul (KR); Oui-Sik Yoo, Seoul (KR); Chan-Eol Kim, Seoul (KR)

(73) Assignee: CORENTEC CO., LTD., Cheonan-si, Chungcheongnam-do (KR)

( * ) Notice: Subject to any disclaimer, the term of this patent is extended or adjusted under 35 U.S.C. 154(b) by 256 days.

(21) Appl. No.: 15/346,534

(22) Filed: Nov. 8, 2016

(65) Prior Publication Data

US 2018/0103961 A1 Apr. 19, 2018

(30) Foreign Application Priority Data

Oct. 13, 2016 (KR) .......................... 10-2016-0132862

(51) Int. Cl.
*A61B 17/15* (2006.01)
*A61F 2/46* (2006.01)

(52) U.S. Cl.
CPC .......... *A61B 17/154* (2013.01); *A61B 17/155* (2013.01); *A61F 2/4684* (2013.01)

(58) Field of Classification Search
CPC ..... A61B 17/15; A61B 17/154; A61B 17/155; A61B 17/157; A61B 17/1764; A61B 17/1675; A61F 2/461; A61F 2/76; A61F 2002/4625; A61F 2002/4658; A61F 2002/4668; A61F 2002/762; A61F 2002/7625; A61F 2002/76
See application file for complete search history.

(56) References Cited

U.S. PATENT DOCUMENTS

| | | | | |
|---|---|---|---|---|
| 5,649,928 A * | 7/1997 | Grundei | ............... | A61B 17/154 606/86 R |
| 6,712,824 B2 * | 3/2004 | Millard | ............... | A61B 17/154 606/87 |
| 8,840,616 B2 * | 9/2014 | Wilkinson | ........... | A61B 17/155 606/88 |
| 9,078,669 B2 * | 7/2015 | Dower | ................. | A61B 17/157 606/88 |
| 2016/0135825 A1 * | 5/2016 | Toler | .................... | A61B 17/025 606/88 |

FOREIGN PATENT DOCUMENTS

KR 10-1515144 B1 4/2015

* cited by examiner

*Primary Examiner* — Kevin T Truong
*Assistant Examiner* — Tracy L Kamikawa
(74) *Attorney, Agent, or Firm* — Workman Nydegger

(57) ABSTRACT

A guide device for knee replacement is configured such that during knee replacement surgery and/or knee replacement revision surgery for implanting a prosthetic knee implant, a degree of external rotation of a femur is identified and aligned through a cut surface of a proximal tibia, then a distance of a gap between the cut surface of the proximal tibia and a cut surface of a distal femur is identified during the surgery, so the degree of external rotation and the distance of the gap are identified simultaneously with one guide device, and thereby it is possible to facilitate the surgery, thereby reducing operation time and minimizing occurrence of a sequela of operation.

16 Claims, 16 Drawing Sheets

GUIDE DEVICE FOR KNEE REPLACEMENT

CROSS REFERENCE TO RELATED APPLICATION

The present application claims priority to Korean Patent Application No. 10-2016-0132862, filed Oct. 13, 2016, the entire contents of which is incorporated herein for all purposes by this reference.

BACKGROUND OF THE INVENTION

Field of the Invention

The present invention relates generally to a guide device for knee replacement. More particularly, the present invention relates to a guide device for knee replacement, the guide device configured such that during knee replacement surgery and/or knee replacement revision surgery for implanting a prosthetic knee implant, a degree of external rotation of a femur is identified and aligned through a cut surface of a proximal tibia, then a distance of a gap between the cut surface of the proximal tibia and a cut surface of a distal femur is identified during the surgery, so the degree of external rotation and the distance of the gap are identified simultaneously with one guide device, and thereby it is possible to facilitate the surgery, thereby reducing operation time and minimizing occurrence of a sequela of operation.

Description of the Related Art

Generally, when a knee joint is severely damaged by arthritis or injury, knee replacement surgery is performed to implant a knee implant instead of the damaged knee joint, which allows normal function of the knee. Further, after the knee replacement surgery, when problems, such as a pain, occur, knee replacement revision surgery is performed.

FIGS. 1 to 3 are reference views illustrating knee replacement; and FIG. 4 is a reference view illustrating a mechanical axis, a transepicondylar axis, and a posterior condylar axis.

Reference will be made to a conventional knee replacement surgery with reference to the accompanying drawings, hereinbelow.

Referring to FIGS. 1 to 4, a tibia 800 is coupled with a tibial component 910; a femur 830 is coupled with a femoral component 920; and a bearing 930 is disposed between the tibial component 910 and the femoral component 920. In order to implant the tibial component 910 and the femoral component 920 into the proximal tibia 810 and the distal femur 840, surgical sites are required to be formed in the proximal tibia 810 and the distal femur 840. To form cut surfaces 820 and 850 of the surgical sites, a standardized cutting guide is used. The cutting guide is a surgical tool for guiding to form the first cut surface 820 of the proximal tibia 810 and the second cut surface 850 of the distal femur 840 by putting the cutting guide on a front surface of the tibia 800 and/or the femur 830 and then inserting a cutting tool into a slit.

Here, the cut surfaces 820 and 850 should be formed to be perpendicular to a mechanical axis M of the tibia in order to allow normal walking after implanting an implant 900 into the knee. Accordingly, as each cutting guide 940, for example, a chamfer cutting guide, which is used to form a bore for allowing the femoral component 920 and the femur 830 to be securely coupled to each other by inserting a stem mounted on a rear surface of the femoral component 920 into the bore, and a box cutting guide, which is used to form the second cut surface 850 perpendicular to the mechanical axis M on the distal femur 840, whenever the chamfer cutting guide and the box cutting guide are put on a front surface of the femur 830, a guide device is required to precisely form the second cut surface 850 and the bore.

The mechanical axis M is an axis of the lower limb, and is perpendicular to both the transepicondylar axis T and the second cut surface 850. Further, the transepicondylar axis T is in parallel to the second cut surface 850, and subtends an angle of 3° with a posterior condylar axis P formed in the posterior condyle, which is a general indicator in the field of orthopedics, so the detailed description thereof will be omitted.

However, when knee replacement surgery and/or knee replacement revision surgery is performed, the transepicondylar axis T may not be identified because of a bone defect of the femur 830. Here, it may be difficult to identify an axis forming the second cut surface 850 through a conventional method of identifying the transepicondylar axis T. Accordingly, a criterion for allowing the degree of external rotation of the femur 830 to be identified is lost, and thus it is impossible to implant the implant 900 by aligning the external rotation.

Further, when knee replacement surgery and/or knee replacement revision surgery is performed, for contact force of the tibial component 910 and the femoral component 920, it is necessary to determine a thickness of the implant 900 to be implanted by identifying the distance of the gap G formed between the first cut surface 820 and the second cut surface 850 during surgery.

However, in the conventional method, when knee replacement surgery and/or knee replacement revision surgery is performed, a step of identifying the degree of external rotation of the femur 830, and another step of identifying the distance of the gap G are generally implemented by using different guide devices, and thus, the process of the surgery becomes complex and difficult. Accordingly, operation time may be long and a sequela of operation may occur.

Korean Patent No. 10-1515144 discloses "Patient specific surgical instrument with cutting guide", which relates generally to a customized surgical instrument used to form a surgical site in the femur or the tibia for allowing the implant to be implanted thereinto, and more specifically, relates to a customized surgical instrument with a cutting guide, the surgical instrument including: a body surrounding a portion of a bone by being connected to the bone; and a cutting guide for guiding a cutting tool that is inserted into the body to form a cut surface of the bone, wherein the body includes a cutting guide insertion part provided at a side of the body, with an insertion hole penetrating through the cutting guide insertion part for allowing the cutting guide to be inserted thereinto; and the cutting guide includes a locking part locked to the body, a guide slot for allowing the cutting tool to be inserted thereinto, and an insertion part inserted into the insertion hole with a predetermined clearance, and thereby it is possible to adjust a location of the cutting guide.

However, even if the above surgical instrument is used, it is impossible to identify the cut surface of the tibia, the cut surface of the femur, and the degree of external rotation of the femur simultaneously with one disclosed surgical instrument, and thus the above described problems may occur.

Thus, a method of implementing a step of identifying the degree of external rotation of the femur 830, and another step of identifying the distance of the gap G, by using one guide device is required in order to reduce operation time through a simple surgical process.

The foregoing is intended merely to aid in the understanding of the background of the present invention, and is not intended to mean that the present invention falls within the purview of the related art that is already known to those skilled in the art.

DOCUMENTS OF RELATED ART (Patent Document 1) Korean Patent No. 10-1515144

SUMMARY OF THE INVENTION

Accordingly, the present invention has been made keeping in mind the above problems occurring in the related art, and the present invention is intended to propose a guide device for knee replacement, the guide device being configured to slide upward and downward during knee replacement surgery and/or knee replacement revision surgery for implanting a prosthetic knee implant so as to identify a distance of a gap formed between a cut surface of a proximal tibia and a cut surface of a distal femur during surgery, and being configured to slide forward and backward so as to identify a degree of external rotation of the distal femur simultaneously, whereby precise surgery is realized and operation time is reduced by using one guide device without additional guide device.

The present invention is further intended to propose a guide device for knee replacement, the guide device being configured to slide upward and downward so as to identify a distance of a gap formed between a cut surface of a proximal tibia and a cut surface of a distal femur during surgery, and being configured to slide forward and backward so as to identify a degree of external rotation of the distal femur during knee replacement surgery and/or knee replacement revision surgery, whereby operation time is reduced by easy use of the guide device.

The present invention is further intended to propose a guide device for knee replacement, the guide device being configured such that during knee replacement revision surgery, when it is impossible to identify a transepicondylar axis (ILA) for identifying a degree of external rotation of a distal femur because of a bone defect, the degree of external rotation of the distal femur is identified based on a cut surface of a proximal tibia, thereby proposing an alternative to the bone defect.

The present invention is further intended to propose a guide device for knee replacement, the guide device being configured to allow additional checking a degree of external rotation based on a cut surface of a proximal tibia, in addition to a conventional method of identifying the degree of external rotation based on a transepicondylar axis during knee replacement surgery, whereby it is possible to perform a precise surgery by double checking the degree of external rotation.

The present invention is further intended to propose a guide device for knee replacement, the guide device being configured to allow a distance of a gap formed between a cut surface of a proximal tibia and a cut surface of a distal femur to be identified during knee replacement surgery and/or knee replacement revision surgery, and to allow a thickness of an implant to be implanted to be easily determined, thereby facilitating surgery.

The present invention is further intended to propose a guide device for knee replacement, the guide device being configured to allow a gap formed between a cut surface of a proximal tibia and a cut surface of a distal femur to be formed in a precise rectangular shape during knee replacement surgery and/or knee replacement revision surgery, and thereby precise surgery is performed and a sequela of operation is prevented by preventing an external rotation of the femur after implanting an implant.

The present invention is further intended to propose a guide device for knee replacement, the guide device being configured such that an external rotation sizing part is in parallel to an up-and-down sliding member such that a gap is formed to be a precise rectangular space through a cut surface of a tibia, and configured to allow a degree of external rotation of a femur to be identified and aligned.

The present invention is further intended to propose a guide device for knee replacement, the guide device being configured such that an external rotation sizing part rotates in an outer direction so as not to interfere with a cutting guide coupled to the front surface of a femur or with an implant.

The present invention is further intended to propose a guide device for knee replacement surgery, the guide device being configured such that a forward sliding limit member that limits forward sliding of a back-and-forth sliding member sliding backward and forward is configured such that a predetermined portion of an uppermost portion of the forward sliding limit member protrudes upward higher than an uppermost portion of an upper body, thereby allowing a surgeon to easily grip the guide device.

The present invention is further intended to propose a guide device for knee replacement, the guide device being configured such that a backward sliding limit member of a back-and-forth sliding member is provided at a location spaced apart from rear ends of horizontal posts by a predetermined distance, and thereby the horizontal posts are easily inserted into a cutting guide and/or a slide accommodation part of an implant.

The present invention is further intended to propose a guide device for knee replacement, the guide device being configured such that vertical posts forming a main body are provided on outer surfaces thereof with a plurality of annular grooves spaced apart from each other at predetermined intervals along a longitudinal direction thereof, thereby allowing intuitively checking a sliding distance of an up-and-down sliding member.

The present invention is further intended to propose a guide device for knee replacement, the guide device being configured to minimize obstruction of a surgeon's view caused by the guide device during surgery by being provided with a first depression part of an upper body and a second depression part of an up-and-down sliding member, and thereby the surgeon's view is easily secured.

In order to achieve the above object, according to one aspect of the present invention, there is provided a guide device for knee replacement, the guide device being configured to slide upward and downward during at least one of knee replacement surgery and/or knee replacement revision surgery for implanting a prosthetic knee implant so as to identify a distance of a gap formed between a first cut surface of a proximal tibia and a second cut surface of a distal femur during surgery, and being configured to slide forward and backward so as to identify a degree of external rotation of the distal femur simultaneously, whereby precise surgery is realized and operation time is reduced.

The guide device for knee replacement may include: an upper body locked to an upper portion of the guide device, and allowing identifying the degree of external rotation of the distal femur during surgery; a main body forming a body of the guide device; a back-and-forth sliding member insertedly coupled to and decoupled from at least one of a cutting guide and the implant by sliding forward and backward, such that at least one of the cutting guide and the implant is coupled to a desired location of the femur; and an up-and-down sliding member seated on the first cut surface at a side thereof, and sliding upward and downward so as to allow the distance of the gap to be identified during surgery.

The upper body may include: a first accommodation part inwardly recessed from opposite sides of the upper body by a predetermined depth; and an external rotation sizing part accommodated in the first accommodation part, and rotatably mounted to the guide device so as to allow identifying and aligning the degree of external rotation of the distal femur during surgery, and the up-and-down sliding member may include: a second accommodation part outwardly recessed from a side of the up-and-down sliding member by a predetermined depth; and a cut surface seat accommodated in the second accommodation part, and rotatably mounted to the guide device so as to be settled on the first cut surface.

The external rotation sizing part may be accommodated in the second accommodation part so as to be in parallel to the up-and-down sliding member while rotating.

The external rotation sizing part may rotate in an outer direction when rotating so as not to interfere with the cutting guide.

The main body may include: vertical posts being in a cylindrical shape and having a predetermined length in a vertical direction; and a first lower limit surface extending such that the vertical posts adjacent to each other are connected to a lower portion of the main body, and the up-and-down sliding member may further include: second lower limit surfaces being in a predetermined shape at opposite sides of a lower portion of the up-and-down sliding member, such that when the up-and-down sliding member slides down over a predetermined distance, the first lower limit surface and the second lower limit surfaces come into contact with each other to prevent the up-and-down sliding member from further sliding down.

The upper body may further include: first upper limit surfaces inwardly provided at opposite sides of a lower surface of the upper body, each of the first upper limit surfaces being a horizontal surface having a predetermined length and width; and the up-and-down sliding member may further include: second upper limit surfaces inwardly provided at opposite sides of an upper surface of the up-and-down sliding member, each of the second upper limit surfaces being a horizontal surface having a predetermined length and width, such that when the up-and-down sliding member slides up over a predetermined distance, the first upper limit surfaces and the second upper limit surfaces come into contact with each other to prevent the up-and-down sliding member from further sliding up.

The second upper limit surfaces may be formed in a reversed L shape and oppositely spaced apart from each other so as to prevent the guide device from blocking a surgeon's view.

The upper body further includes: first through-holes formed through opposite sides of a front surface of the upper body from the front to the rear, and The back-and-forth sliding member may further include: horizontal posts horizontally provided to be in a cylindrical shape, and accommodated in the first through-holes so as to allow the back-and-forth sliding member to slide forward and backward; and a forward sliding limit member allowing front ends of the horizontal posts adjacent to each other to be connected to each other, such that when the back-and-forth sliding member slides forward over a predetermined distance, the forward sliding limit member comes into contact with the front surface of the upper body, thereby preventing the back-and-forth sliding member from further sliding forward.

The forward sliding limit member may be configured such that when the forward sliding limit member comes into contact with the upper body, a predetermined portion of an uppermost portion of the forward sliding limit member protrudes upward higher than an uppermost portion of the upper body, thereby allowing a surgeon to easily grip the guide device.

The back-and-forth sliding member may further include: a backward sliding limit member allowing rear ends of the horizontal posts adjacent to each other to be connected to each other such that when the back-and-forth sliding member slides backward over a predetermined distance, the backward sliding limit member comes into contact with a rear surface of the upper body, thereby preventing the back-and-forth sliding member from further sliding backward.

The backward sliding limit member may be provided at a location spaced apart from the rear ends of the horizontal posts by a predetermined distance such that the horizontal posts are inserted into at least one of the cutting guide and a slide accommodation part of the implant.

The vertical posts may be provided on outer surfaces thereof with a plurality of annular grooves spaced apart from each other at predetermined intervals along a longitudinal direction thereof, thereby allowing the distance of the gap to be quickly identified by checking a sliding distance of the up-and-down sliding member.

The upper body may further include: a first depression part provided by being upwardly depressed from inside edges of the first upper limit surfaces to a predetermined height, such that a surgeon's view is secured.

The up-and-down sliding member may further include: a second depression part provided by being upwardly depressed from inside edges of the second lower limit surfaces by a predetermined height, such that a surgeon's view is secured.

According to the above embodiments and description to be described hereinafter, the present invention is advantageous for the following reasons.

The present invention is advantageous in that it is configured to slide upward and downward during at least one of knee replacement surgery and/or knee replacement revision surgery for implanting a prosthetic knee implant so as to identify a distance of a gap formed between a cut surface of a proximal tibia and a cut surface of a distal femur during surgery, and being configured to slide forward and backward so as to identify a degree of external rotation of the distal femur simultaneously, whereby precise surgery is realized and operation time is reduced by using one guide device without additional guide device.

The present invention is further advantageous in that it is configured to slide upward and downward so as to identify a distance of a gap formed between a cut surface of a proximal tibia and a cut surface of a distal femur during surgery, and being configured to slide forward and backward so as to identify a degree of external rotation of the distal femur during knee replacement surgery and/or knee replacement revision surgery, whereby operation time is reduced by easy use of the guide device.

The present invention is further advantageous in that it is configured such that during knee replacement revision surgery, when it is impossible to identify a transepicondylar axis (TEA) for identifying a degree of external rotation of a distal femur because of a bone defect, the degree of external rotation of the distal femur is identified based on a cut surface of a proximal tibia, thereby proposing an alternative to the bone defect.

The present invention is further advantageous in that it is configured to allow additional checking a degree of external rotation based on a cut surface of a proximal tibia, in addition to a conventional method of identifying the degree of external rotation based on a transepicondylar axis during knee replacement surgery, whereby it is possible to perform a precise surgery by double checking the degree of external rotation.

The present invention is further advantageous in that it is configured to allow a distance of a gap formed between a cut surface of a proximal tibia and a cut surface of a distal femur to be identified during knee replacement surgery and/or knee replacement revision surgery, and to allow a thickness of an implant to be implanted to be easily predicted, thereby facilitating surgery.

The present invention is further advantageous in that it is configured to allow a gap formed between a cut surface of a proximal tibia and a cut surface of a distal femur to be formed in a precise rectangular shape during knee replacement surgery and/or knee replacement revision surgery, and thereby precise surgery is performed and a sequela of operation is prevented by preventing an external rotation of the femur after implanting an implant.

The present invention is further advantageous in that it is configured such that an external rotation sizing part is in parallel to an up-and-down sliding member such that a gap is formed to be a precise rectangular space through a cut surface of a tibia, and configured to allow a degree of external rotation of a femur to be identified and aligned.

The present invention is further advantageous in that it is configured such that an external rotation sizing part rotates in an outer direction so as not to interfere with a cutting guide coupled to the front surface of a femur or with an implant.

The present invention is further advantageous in that it is configured such that a forward sliding limit member that limits forward sliding of a back-and-forth sliding member sliding backward and forward is configured such that a predetermined portion of an uppermost portion of the forward sliding limit member protrudes upward higher than an uppermost portion of an upper body, thereby allowing a surgeon to easily grip the guide device.

The present invention is further advantageous in that it is configured such that a backward sliding limit member of a back-and-forth sliding member is provided at a location spaced apart from rear ends of horizontal posts by a predetermined distance, and thereby the horizontal posts are easily inserted into a cutting guide and/or a slide accommodation part of an implant.

The present invention is further advantageous in that it is configured such that vertical posts forming a main body are provided on outer surfaces thereof with a plurality of annular grooves spaced apart from each other at predetermined intervals along a longitudinal direction thereof, thereby allowing intuitively checking a sliding distance of an up-and-down sliding member.

The present invention is further advantageous in that it is configured to minimize obstruction of a surgeon's view caused by the guide device during surgery by being provided with a first depression part of an upper body and a second depression part of an up-and-down sliding member, and thereby the surgeon's view is easily secured.

BRIEF DESCRIPTION OF THE DRAWINGS

The above and other objects, features, and other advantages of the present invention will be more clearly understood from the following detailed description when taken in conjunction with the accompanying drawings, in which.

DETAILED DESCRIPTION OF THE INVENTION

Figure 1:
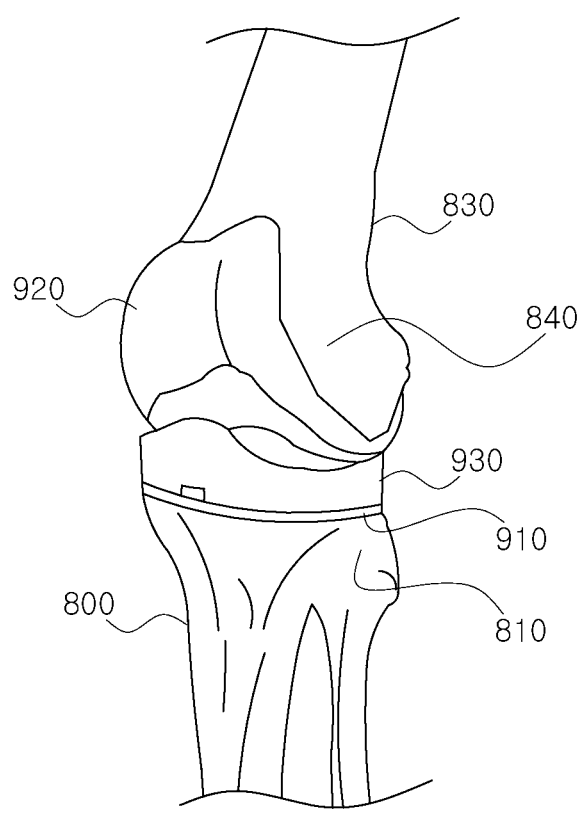
FIGS. 1 to 3 are reference views illustrating knee replacement.
Figure 2:
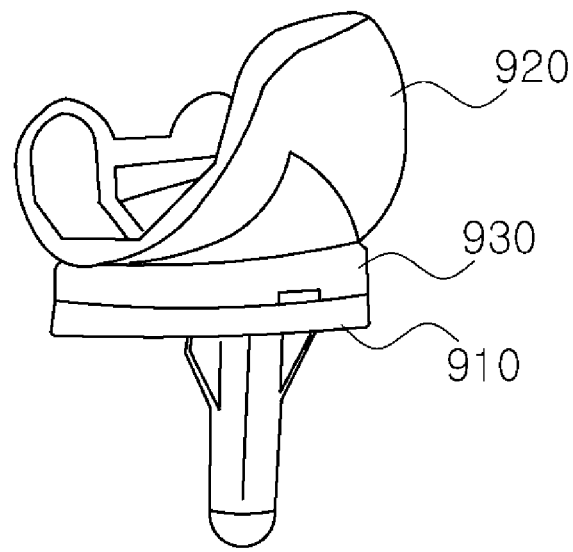
Figure 3:
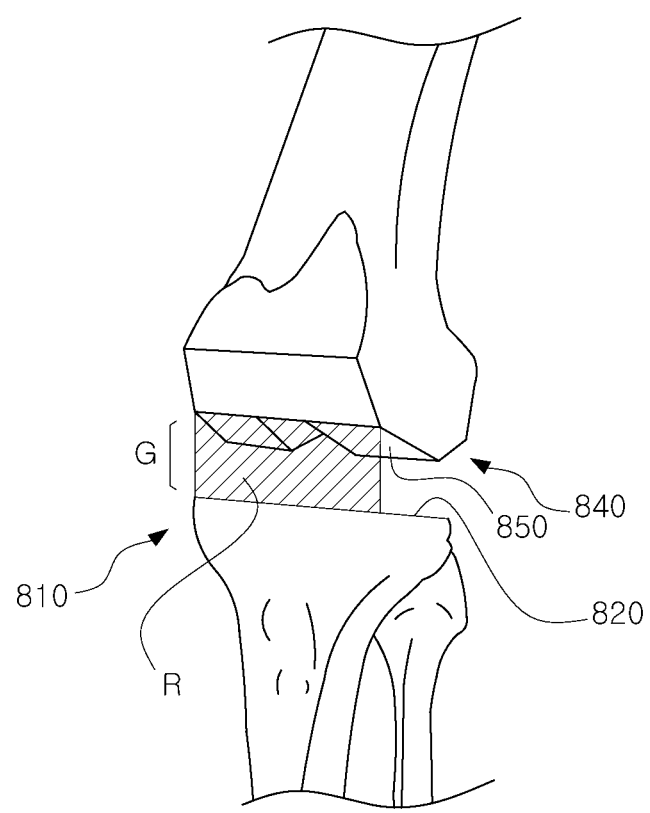

Hereinbelow, exemplary embodiments of the present invention will be described in detail with reference to the accompanying drawings. Throughout the drawings, the same reference numerals will refer to the same or like parts.

In the description, the term "forward direction" refers to a direction where the anterior knee faces a surgeon; "backward direction" refers to a direction where the anterior knee faces away from the surgeon, that is, a direction opposite to the forward direction. Further, "inner direction" refers to a direction facing a vertical line passing from opposite sides of the device to the center thereof; "outer direction" refers to a direction opposite to the inner direction. Further, the term "implant 900" used herein is intended to include an implant trial that is inserted into the knee joint in advance, to determine a size of the implant 900.

Figure 5:
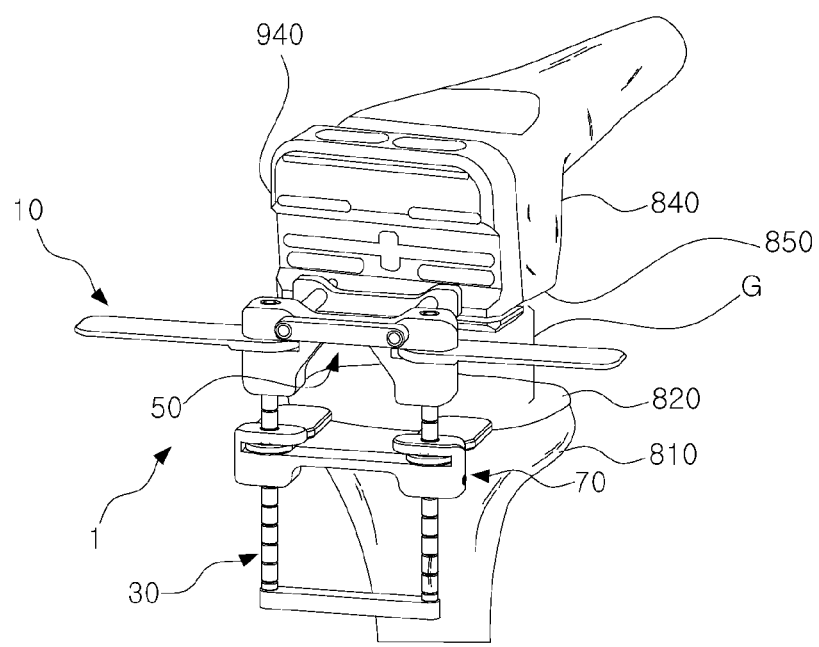
FIG. 5 is a perspective view illustrating a state where a guide device for knee replacement according to an embodiment of the present invention is coupled to a cutting guide.
Figure 6:
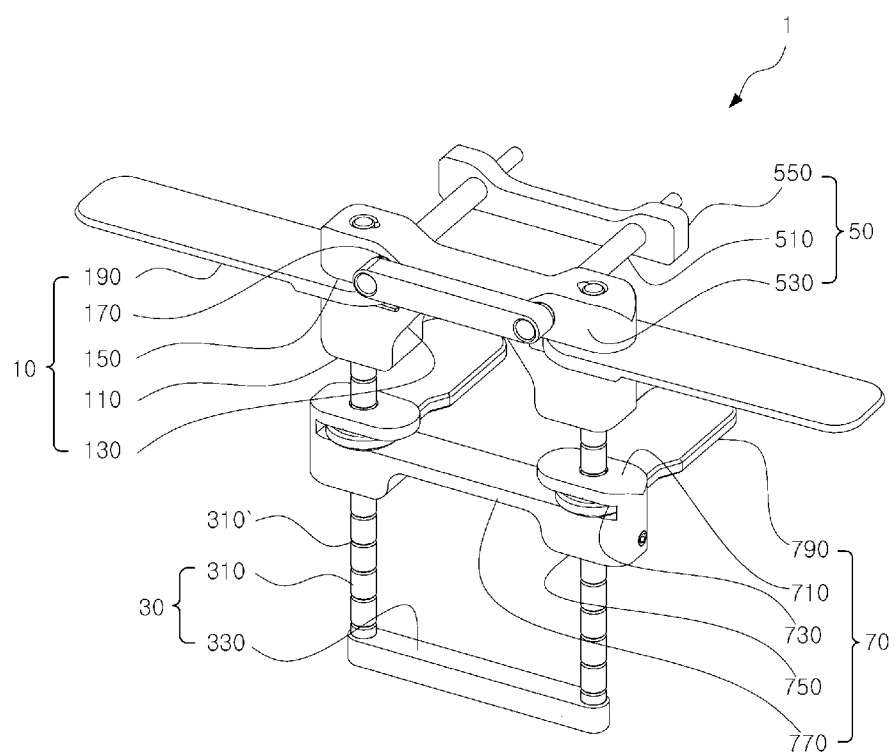
FIG. 6 is a perspective front view illustrating a guide device for knee replacement according to the embodiment of the present invention.
Figure 7:
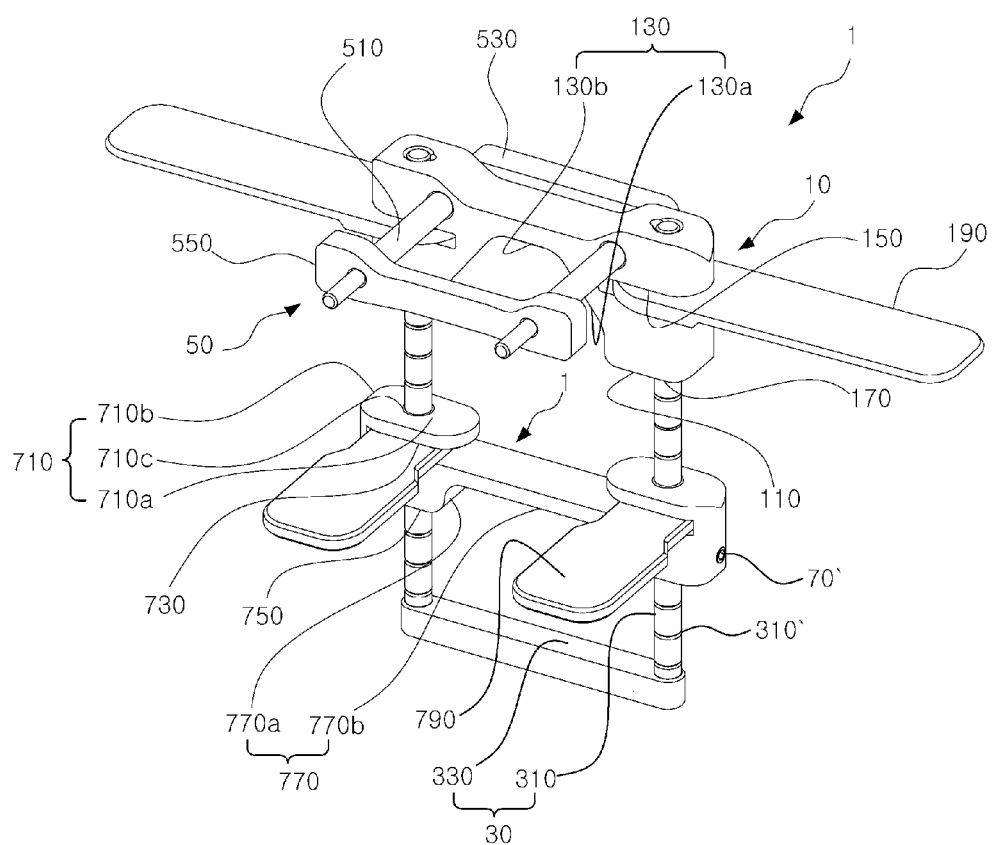
FIG. 7 is a perspective rear view illustrating the guide device for knee replacement according to FIG. 6.
Figure 8:
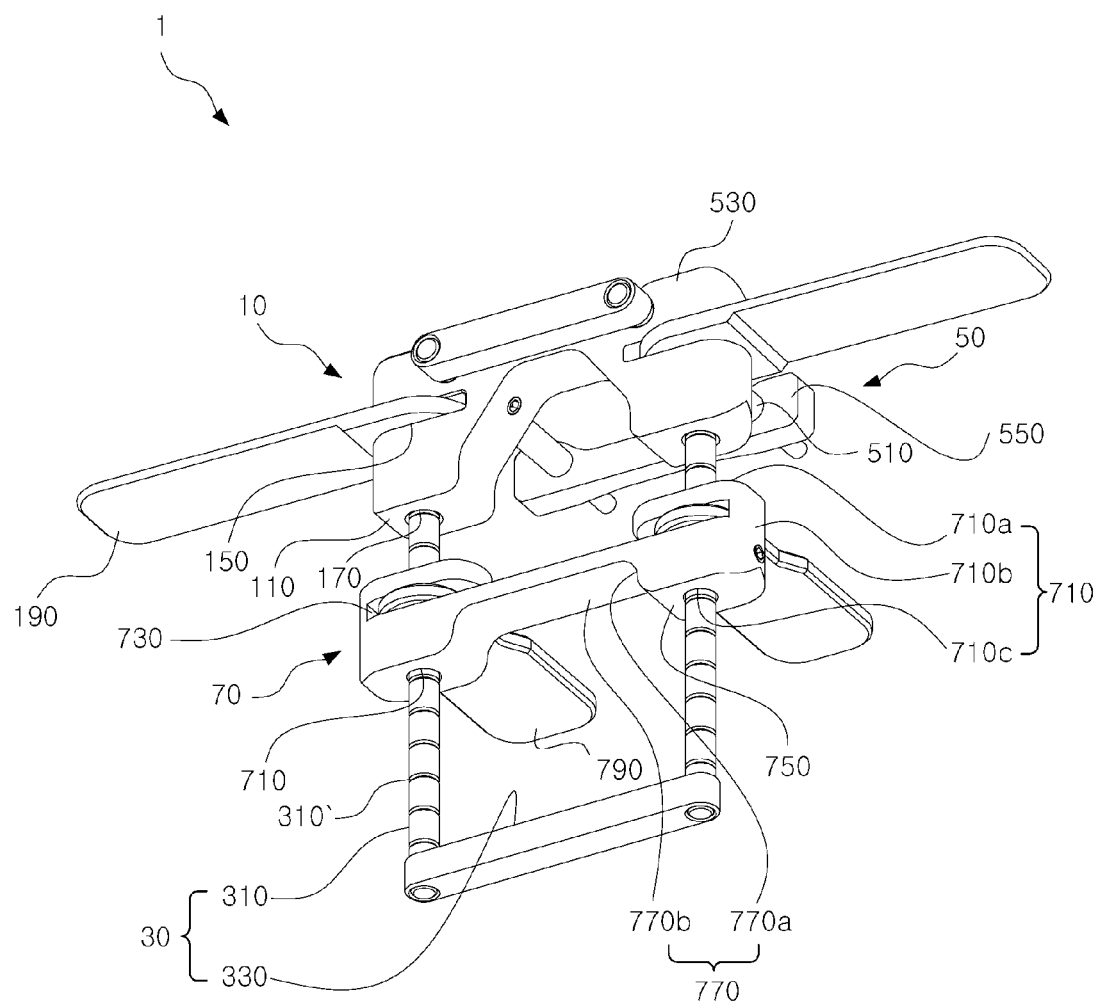
FIG. 8 is a perspective bottom view illustrating the guide device for knee replacement according to FIG. 6.
Figure 9A:
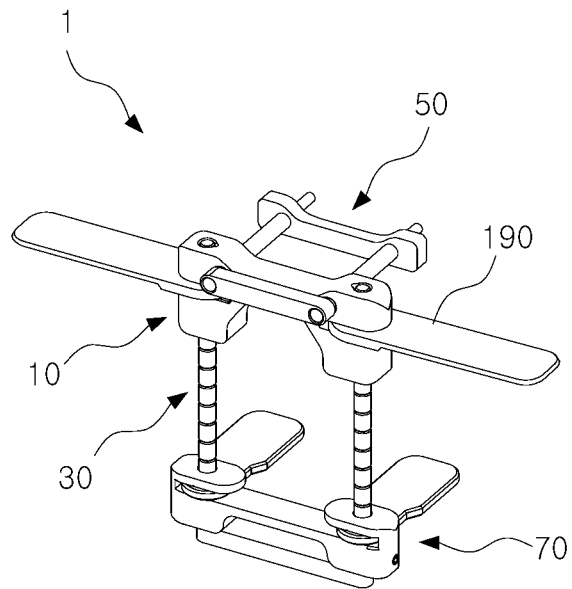
FIGS. 9A, 9B, and 9C are reference views illustrating a rotation of an external rotation sizing part according to FIG. 6.
Figure 9B:
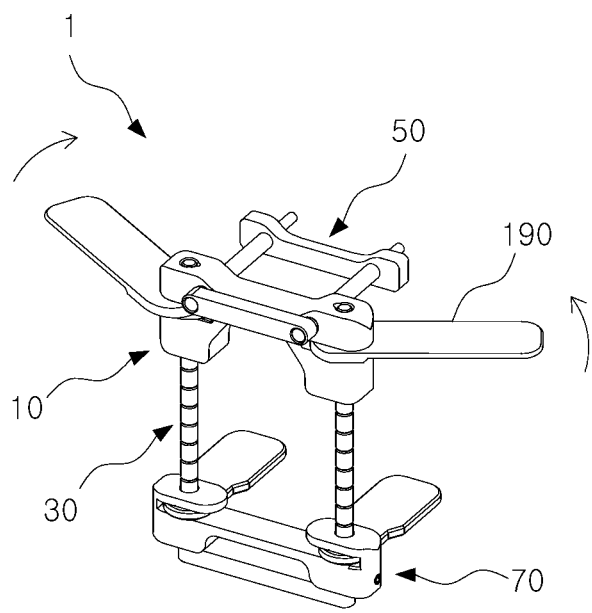
Figure 9C:
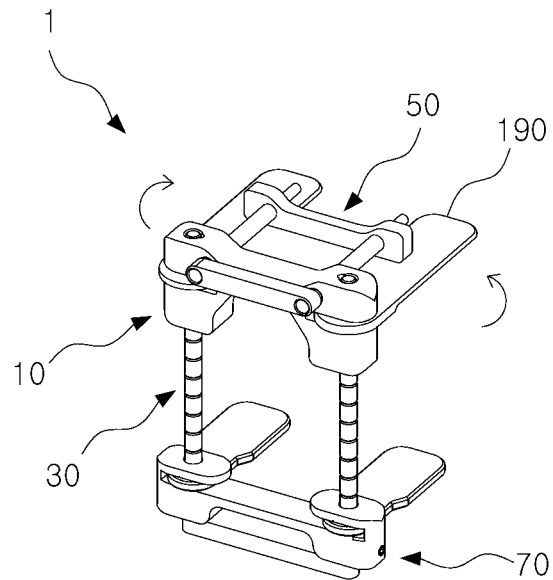
Figure 10A:
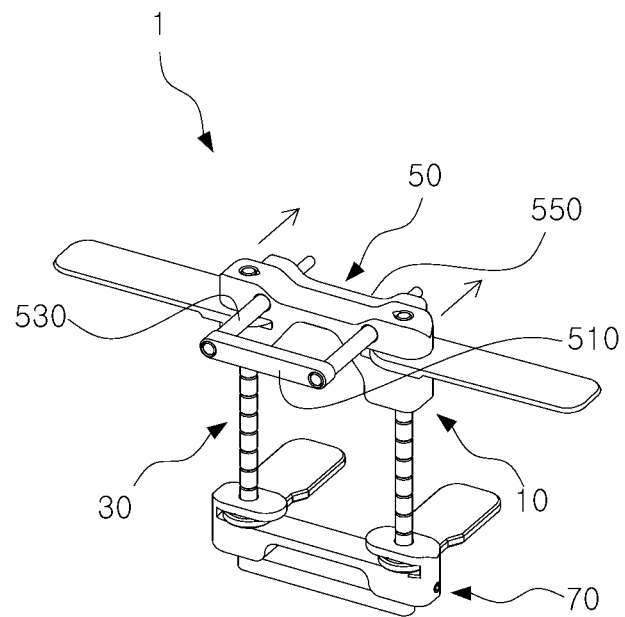
FIGS. 10A, 10B, and 10C are reference views illustrating sliding of a back-and-forth sliding member according to FIG. 6.
Figure 10B:
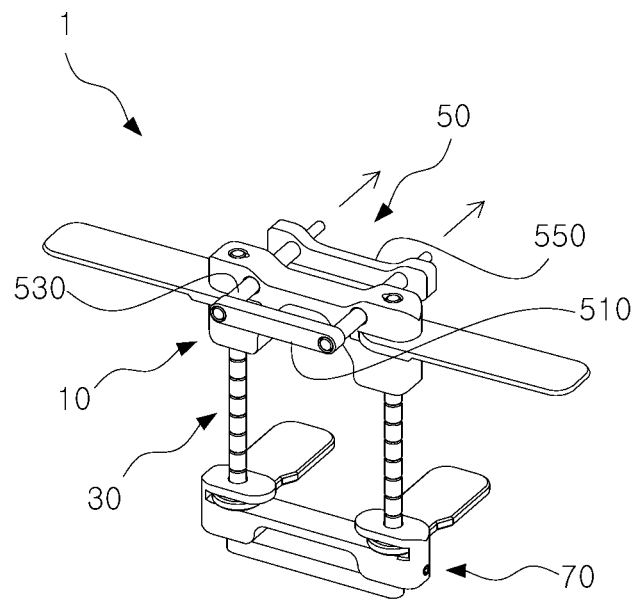
Figure 10C:
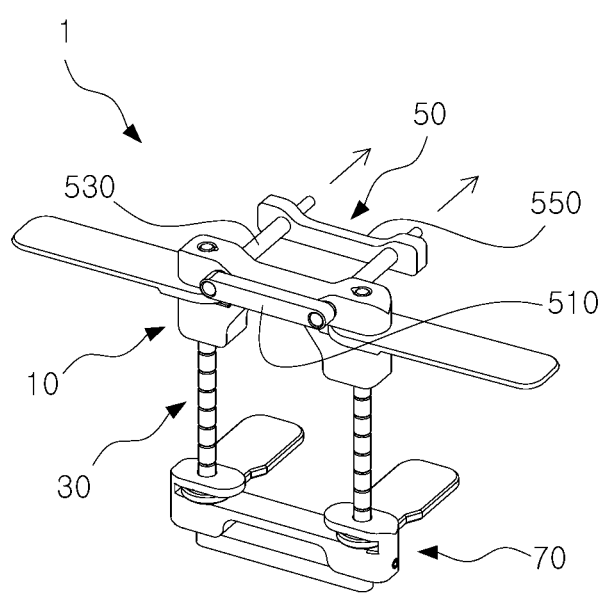
Figure 11A:
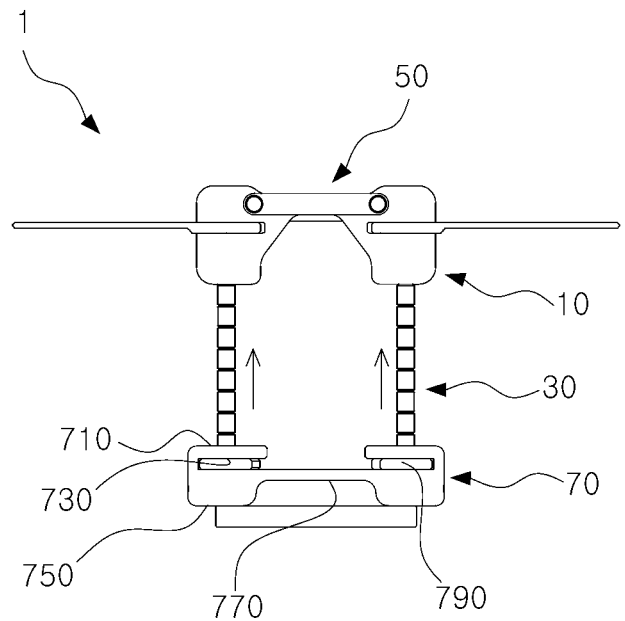
FIGS. 11A, 11B, and 11C are reference views illustrating sliding of an up-and-down sliding member according to FIG. 6.
Figure 11B:
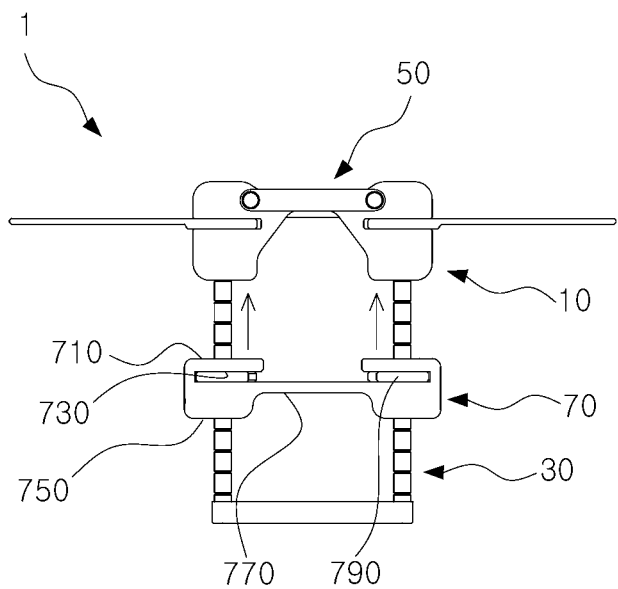
Figure 11C:
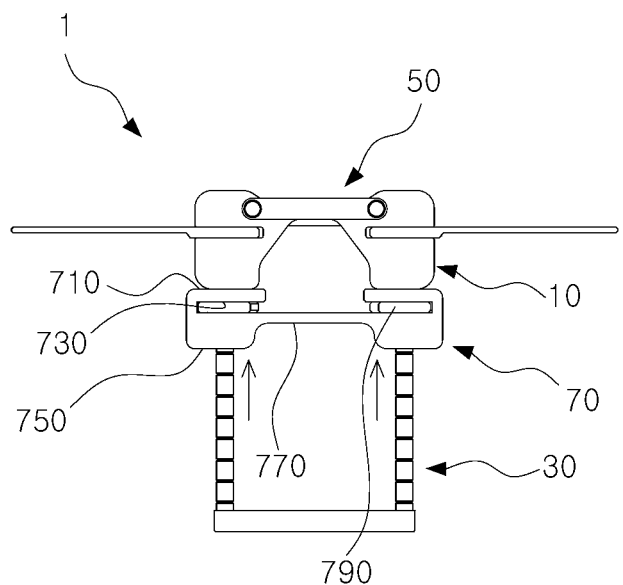
Figure 12A:
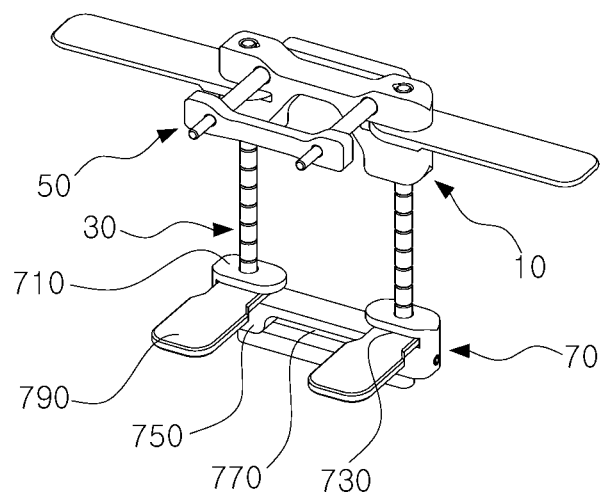
FIGS. 12A, 12B, and 12C are reference views illustrating a rotation of a cut surface seat according to FIG. 6.
Figure 12B:
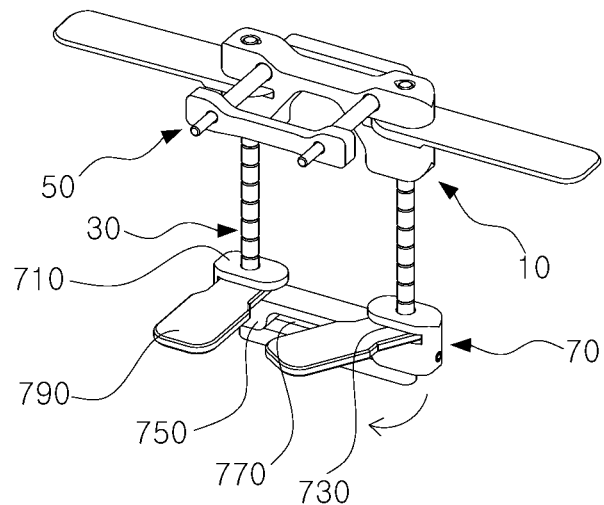
Figure 12C:
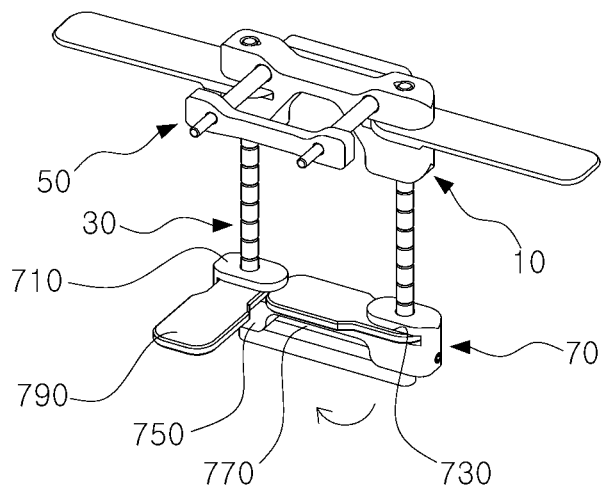

FIG. 5 is a perspective view illustrating a state where a guide device for knee replacement according to an embodiment of the present invention is coupled to a cutting guide; FIG. 6 is a perspective front view illustrating a guide device for knee replacement according to an embodiment of the present invention; FIG. 7 is a perspective rear view illustrating the guide device for knee replacement according to FIG. 6; FIG. 8 is a perspective bottom view illustrating the guide device for knee replacement according to FIG. 6; FIGS. 9A, 9B, and 9C are reference views illustrating a rotation of an external rotation sizing part according to FIG. 6; FIGS. 10A, 10B, and 10C are reference views illustrating sliding of a back-and-forth sliding member according to FIG. 6; FIGS. 11A, 11B, and 11C are reference views illustrating sliding of an up-and-down sliding member according to FIG. 6; and FIGS. 12A, 12B, and 12C are reference views illustrating a rotation of a cut surface seat according to FIG. 6.

Figure 4:
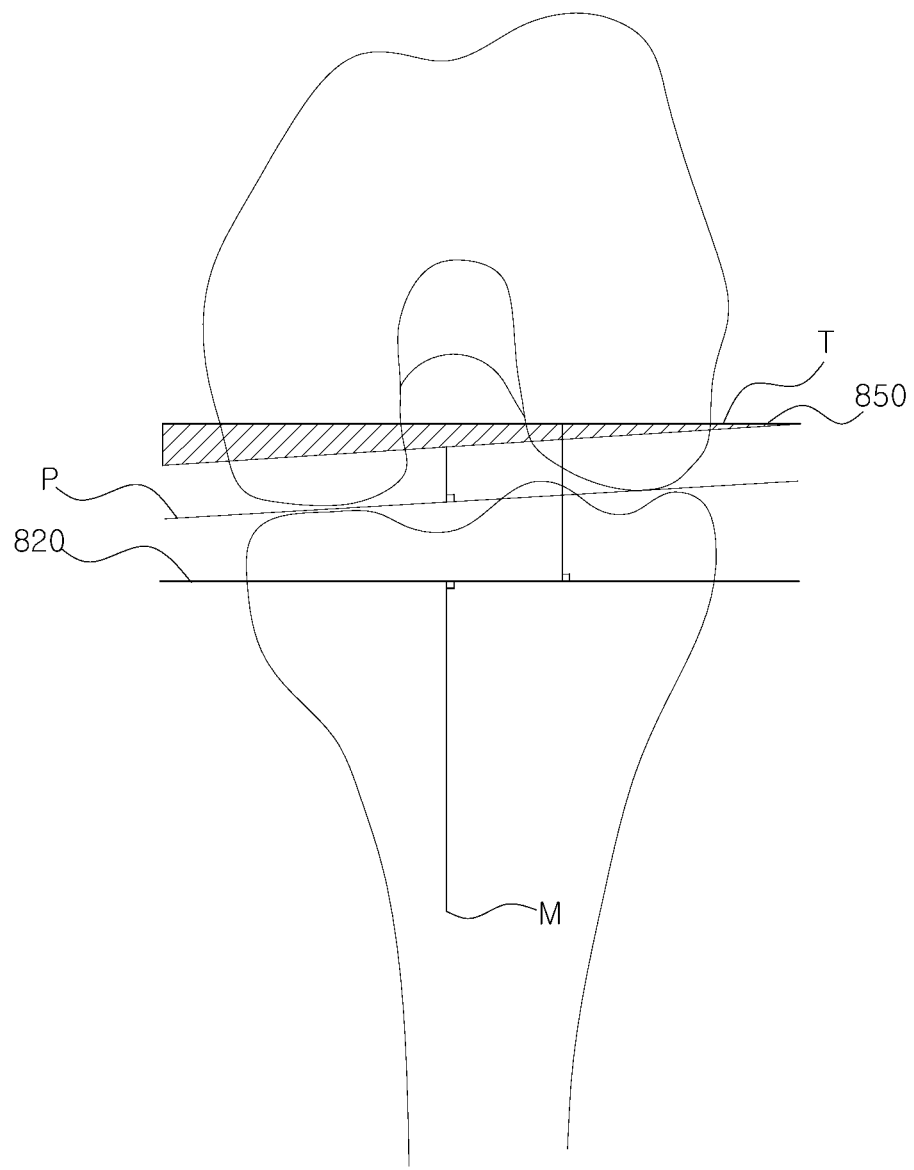
FIG. 4 is a reference view illustrating a mechanical axis, a transepicondylar axis, and a posterior condylar axis.

Referring to FIG. 4, a guide device 1 for knee replacement according to an embodiment of the present invention relates to a device for assisting knee replacement surgery and/or knee replacement revision surgery, the device being configured to allow identifying and aligning both a distance of a gap G formed between a first cut surface 820 of a proximal tibia 810 and a second cut surface 850 of a distal femur 840, and a degree of external rotation of the distal femur 840 during knee replacement surgery when the second cut surface 850 is formed on the distal femur 840 in order to implant a prosthetic knee implant 900 into a patient's body by using a cutting guide 940, and thereby it is possible to perform a precise surgery and reduce operation time, and accordingly, it is possible to minimize bleeding of the patient and possible to prevent a sequela of operation. To achieve this, the guide device for knee replacement 1 may include: an upper body 10, a main body 30, a back-and-forth sliding member 50, and an up-and-down sliding member 70.

The upper body 10 is locked to an upper part of the guide device 1, such that the gap G and the degree of external rotation of the distal femur 840 are identified and aligned during surgery, and thereby it is possible to fix the implant 900 (a tibial component or a tibial component trial 910, a femoral component or a femoral component trial 920, and a bearing 930) and/or the cutting guide 940 for forming the second cut surface 850 and/or a bore 880, at a desired location of a femur 830 at a desired angle. Accordingly, by the upper body 10, a height of the gap G for implantation of the implant 900 is measured during surgery, then a thickness of the implant 900 to be implanted is predicted, and the gap G is formed to be a rectangular space R having an appropriate distance. Thereby the implant 900 is implanted without external rotation and securely fixed, and thus it is possible to prevent a sequela of operation from occurring. Further, a shape of the upper body 10 is not limited to a predetermined shape, but it is preferred that the upper body has a rectangular cross-section from a front view, and a first side of a lower surface thereof is upwardly depressed by a predetermined height. To achieve this, the upper body 10 may include first upper limit surfaces 110, a first depression part 130, a first accommodation part 150, first through-holes 170, and an external rotation sizing part 190.

The first upper limit surfaces 110 are inwardly provided at opposite sides of a lower surface of the upper body 10, and each of the first upper limit surfaces is a horizontal surface having a predetermined length and width. To be more specific, the first upper limit surfaces 110 prevent the up-and-down sliding member 70 from further sliding up by coming into contact with a second upper limit surfaces 710 of the up-and-down sliding member 70. Further, the shapes of the first upper limit surfaces 110 are an example for the purpose of describing the present invention, but not limited to the above described shape.

The first depression part 130 is formed in a second side of the lower surface of the upper body 10, and preferably, is provided by being upwardly depressed from inside edges of the first upper limit surfaces 110 to a predetermined height, such that a surgeon's view is secured. With the assistance of the guide device 1, when the cutting guide 940 and/or the implant trial 900 is coupled to the femur 830, the surgeon's view faces a front side of the guide device 1, and thus it is preferred that the first depression part 130 is formed to prevent the surgeon's view from being blocked by the guide device 1. To achieve this, the first depression part 130 may include first inclined portions 130a and a first horizontal portion 130b.

The first inclined portions 130a are upwardly inclined from the second side of the lower surface of the upper body 10 to a center thereof at a predetermined angle. For example, the first inclined portions 130a may be upwardly inclined from the inside edges of the first upper limit surfaces 110. Further, the first inclined portions 130a may be formed by vertically extending from the lower surface of the upper body, but not limited thereto.

The first horizontal portion 130b is formed by horizontally extending from inside ends of the first inclined portions 130a. Accordingly, it is possible to minimize obstruction of the surgeon's view thanks to the first depression part 130 constituted by both the first inclined portions 130a and the first horizontal portion 130b. The shape of the first horizontal portion 130b is an example, and may be formed to be other shapes.

The first accommodation part 150 is inwardly recessed from opposite sides of the upper body 10 by a predetermined depth so as to allow the degree of external rotation of the distal femur 840 to be identified during surgery. To be more specific, the first accommodation part 150 accommodates an external rotation sizing part 190 therein such that the external rotation sizing part 190 is in parallel to a cut surface seat 790 while rotating, whereby the degree of external rotation of the distal femur 840 is identified and aligned. The shape of the first accommodation part 150 is not limited to a predetermined shape, but it is preferred that the first accommodation part has a "⊏" shaped cross-section.

The first through-holes 170 are formed through opposite sides of a front surface of the upper body 10 from the front to the rear. The number of the first through-holes 170 is not limited to a predetermined number, but it is preferred that the first through-holes are provided two in number at locations bilaterally symmetrical with each other, such that two horizontal posts 510 of a back-and-forth sliding member 50 are inserted into the first through-holes, thereby guiding sliding of the back-and-forth sliding member 50.

The external rotation sizing part 190 is accommodated in the first accommodation part 150, and is rotatably mounted to the guide device 1, wherein it is preferred that the external rotation sizing part is inserted into the first accommodation part to be leveled while rotating in an outer direction, thereby allowing the degree of external rotation of the distal femur 840 to be identified and aligned during surgery. Further, it is preferred that the external rotation sizing part 190 is formed to be in a rectangular planar shape. As described above, the external rotation sizing part 190 is locked to be in parallel to the cut surface seat 790, and the cut surface seat 790 is seated on the first cut surface 820 to be in parallel to the transepicondylar axis T formed in a direction perpendicular to the mechanical axis M. Thereby, by using the external rotation sizing part 190, it is possible to identify the degree of external rotation of the distal femur 840 during surgery. This configuration allows additional checking the degree of external rotation through the first cut surface 820 in addition to a conventional method of identifying the degree of external rotation by leveling with the transepicondylar axis T, whereby it is possible to perform a precise surgery and/or possible to implant the implant by double checking the degree of external rotation.

Further, when it is impossible to identify the transepicondylar axis T because of a bone defect, during the knee replacement revision surgery, the present invention may propose an alternative to this case by allowing the degree of external rotation to be identified by using the external rotation sizing part 190. Further, each external rotation sizing part 190 is accommodated in each sizing part accommodation part 950 of the cutting guide 940 such that the second cut surface 850 is formed to be in parallel to the first cut surface 820 through the cutting guide 940, and thereby it is possible to form the rectangular space R suitable for the gap G. Thus, the external rotation sizing part is configured to rotate in an outer direction so as not to interfere with the cutting guide 940 when and the external rotation sizing part is accommodated in the sizing part accommodation part 950 (see FIG. 14A). Thereby, the external rotation sizing part 190 is locked to the first accommodation part 150 while being in parallel to the cut surface seat 790. The external rotation sizing part 190 may include an accommodation hole provided through a side thereof, and preferably, the accommodation hole is formed through from the top to the bottom of the external rotation sizing part so as to accommodate vertical posts 310 such that the external rotation sizing part 190 rotates in the state where the external rotation sizing part is securely locked to the first accommodation part 150. The accommodation hole is formed through each external rotation sizing part 190, and the number thereof is not limited to a predetermined number, but it is preferred that two external rotation sizing parts 190 are respectively provided with one accommodation hole.

The main body 30 forms a body of the guide device 1, and may include the vertical posts 310 and the first lower limit surface 330.

The vertical posts 310 are in a cylindrical shape and have a predetermined length in a vertical direction, with the upper body 10 being locked to the top of the vertical posts, wherein the vertical posts are accommodated in the up-and-down sliding member 70 so as to guide up-and-down sliding of the up-and-down sliding member 70. It is preferred that the vertical posts 310 are provided two in number at opposite side of the guide device. Further, the vertical posts 310 are provided on outer surfaces thereof with a plurality of annular grooves 310' spaced apart from each other at predetermined intervals along a longitudinal direction thereof, thereby allowing the distance of the gap G to be quickly identified. Further, each of the second upper limit surfaces 710 of the up-and-down sliding member 70 is formed with a first post accommodation hole 710c having the roughly same diameter as the vertical posts 310, in order to accommodate the vertical posts 310, and thereby the first post accommodation hole is engaged with one of the annular grooves 310' in response to up-and-down sliding of the up-and-down sliding member 70, thereby allowing the surgeon to easily use the guide device.

The first lower limit surface 330 is formed by extending such that the vertical posts 310 adjacent to each other are connected to a lower portion of the main body 30, and thereby when the up-and-down sliding member 70 slides down a predetermined distance, the first lower limit surface 330 and the second lower limit surfaces 790 come into contact with each other to prevent the up-and-down sliding member 70 from further sliding down.

Referring to FIGS. 3 to 5 and 9A to 9C, the back-and-forth sliding member 50 is insertedly coupled to and decoupled from the cutting guide 940, such that the cutting guide 940 allows the second cut surface 850 to be formed at a desired location of the femur 830 and/or a thickness of the implant 900 to be implanted to be predicted. For example, when the guide device 1 is coupled to the cutting guide 940, a side of the back-and-forth sliding member 50 is inserted into the first through-holes 170, and slides forward and backward by a predetermined distance to be coupled to and decoupled from a slide accommodation part 960 of the cutting guide 940, such that the cutting guide 940 is allowed to form the second cut surface 850 at a desired location of the femur 830. To achieve this, the back-and-forth sliding member 50 may include horizontal posts 510, a forward sliding limit member 530, and a backward sliding limit member 550.

The horizontal posts 510 allow the back-and-forth sliding member 50 to slide forward and backward and to be easily coupled to and decoupled from the cutting guide 940. The shape of the horizontal post is not limited to a predetermined shape, but it is preferred that the horizontal post horizontally extends in a cylindrical shape. For example, the horizontal posts 510 may be provided two in number at locations corresponding to the first through-holes 170, and slide forward through the first through-holes 170 to be coupled to the cutting guide 940 by being accommodated in the slide accommodation part 960, and on the contrary, slide backward to be decoupled from the cutting guide 940.

The forward sliding limit member 530 allows front ends of the horizontal posts 510 adjacent to each other to be connected to each other. Preferably, the front ends of the horizontal posts 510 horizontally extend to prevent the back-and-forth sliding member 50 from further sliding forward. To be more specific, when the back-and-forth sliding member 50 slides forward over a predetermined distance, the forward sliding limit member 530 comes into contact with the front surface of the upper body 10, thereby preventing the back-and-forth sliding member 50 from further sliding forward.

In addition, it is preferred that the forward sliding limit member 530 is configured such that when the forward sliding limit member 530 comes into contact with the upper body 10, a predetermined portion of an uppermost portion of the forward sliding limit member 530 protrudes upward higher than an uppermost portion of the upper body 10, thereby allowing the surgeon to easily grip the back-and-forth sliding member 50.

The backward sliding limit member 550 allows rear ends of the horizontal posts 510 adjacent to each other to be connected to each other. Preferably, the rear ends of the horizontal posts 510 horizontally extend to prevent the back-and-forth sliding member 50 from further sliding backward. To be more specific, the backward sliding limit member 550 laterally connects two horizontal posts 510 together such that when the back-and-forth sliding member 50 slides backward over a predetermined distance, the backward sliding limit member 550 comes into contact with a rear surface of the upper body 10, thereby preventing the back-and-forth sliding member 50 from further sliding backward. In addition, it is preferred that the backward sliding limit member 550 is provided at a location spaced apart from the rear ends of the horizontal posts 510 by a predetermined distance such that the horizontal posts 510 are inserted into the slide accommodation part 960 of the cutting guide 940.

Referring to FIGS. 3 to 5 and 10A to 10C, the up-and-down sliding member 70 is settled on the first cut surface 820 of the tibia 800 on a side thereof, and allows identifying a height of the gap G by sliding upward and backward by a predetermined distance. As described above, during knee replacement surgery and/or knee replacement revision surgery, it is necessary to identify the height of the gap G formed between the first cut surface 820 and the second cut surface 850 in order to implant the implant 900 having a suitable thickness. Accordingly, by checking the distance between the up-and-down sliding member 70 and the upper body 10, it is possible to couple the cutting guide 940 at a desired location, and possible to implant the implant 900 having a appropriate size, and thereby it is possible to perform precise and quick knee replacement surgery and/or knee replacement revision surgery. Further, the up-and-down sliding member 70 may be formed at a side thereof with a coupling means accommodation hole 70' in order to lock the up-and-down sliding member to the vertical posts 310 at a predetermined height, wherein a coupling means may be engaged with the accommodation hole 70' to compress the vertical posts 310, thereby locking the up-and-down sliding member 70 to the vertical posts. To achieve this, the up-and-down sliding member 70 may include the second upper limit surfaces 710, a second accommodation part 730, second lower limit surfaces 750, and a second depression part 770.

The second upper limit surfaces 710 form an upper surface of the up-and-down sliding member 70 and prevent the up-and-down sliding member 70 from further sliding up. To be more specific, when the up-and-down sliding member 70 slides up over a predetermined distance, the second upper limit surfaces 710 and the first upper limit surfaces 110 may come into contact with each other to prevent the up-and-down sliding member 70 from further sliding up. Further, it is preferred that the second upper limit surfaces 710 are provided at locations of the up-and-down sliding member 70 adjacent to the vertical posts 310, thereby minimizing obstruction of the surgeon's view caused by the guide device 1. In other words, it is preferred that the second upper limit surfaces 710 are formed in a reversed L shape and oppositely spaced apart from each other. To achieve this, the second upper limit surfaces 710 may include a contact part 710a, a vertical part 710b, and the first post accommodation hole 710c.

The contact part 710a forms an horizontal upper surface of each of the second upper limit surfaces 710 so as to come into direct contact with the first upper limit surfaces 110.

The vertical part 710b downwardly extends from the outer edge of the contact part 710a by a predetermined length. Accordingly, by the contact part 710a and the vertical part 710b, the second upper limit surfaces 710 are formed in a reversed L shape at opposite sides of the up-and-down sliding member.

The first post accommodation hole 710c is formed through each of the second upper limit surfaces 710 from the top to the bottom thereof to accommodate the vertical posts 310 therein.

The second accommodation part 730 is formed by being outwardly recessed from a side of the up-and-down sliding member 70 by a predetermined depth, and preferably, the second accommodation part is an inner space defined by the reversed L shaped second upper limit surfaces 710, wherein the second accommodation part accommodates a cut surface seat 790 therein. Since the second accommodation part 730 is outwardly recessed from the inside by a predetermined depth, unlike the first accommodation part 150, the cut surface seat 790 is capable of rotating in an inner direction of the guide device 1. In addition, in order not to interfere with a rotation of a cut surface seat 790 accommodated in the second accommodation part 730 by a neighboring cut surface seat 790 accommodated in the second accommodation part 730, it is preferred that the neighboring second accommodation parts 730 are spaced apart from each other by a distance suitable for allowing a rotation of the cut surface seat 790.

The second lower limit surfaces 750 are in a predetermined shape at opposite sides of a lower portion of the up-and-down sliding member 70 to prevent the up-and-down sliding member 70 from further sliding down. To be more specific, when the up-and-down sliding member 70 slides down a predetermined distance, the first lower limit surface 330 and the second lower limit surfaces 750 come into contact with each other to prevent the up-and-down sliding member from further sliding down. Further, it is preferred that each of the second lower limit surfaces 750 is a horizontal surface having a predetermined length and width.

The second depression part 770 is formed in a second side of the lower surface of the up-and-down sliding member 70, and preferably, is provided by being upwardly depressed from inside edges of the second lower limit surfaces 750 by a predetermined height, such that the surgeon's view to the surgical site is secured. As described above, with the assistance of the guide device 1, when the cutting guide 940 and/or the implant 900 is coupled to the femur 830, the surgeon's view faces the front side of the guide device 1, and thus it is preferred that the second depression part 770 is formed to prevent the surgeon's view from being blocked by the guide device 1. To achieve this, the second depression part 770 may include second inclined portions 770a and a second horizontal portion 770b.

The second inclined portions 770a are formed by being upwardly inclined from the second side of the lower surface of the up-and-down sliding member 70, and preferably, upwardly inclined from the inside edges of the second lower limit surfaces 750 toward the center of the up-and-down sliding member. Further, unlike the above configuration, the second inclined portions 770a may be formed by vertically extending from the lower surface of the up-and-down sliding member, but not limited thereto.

The second horizontal portion 770b is formed by horizontally extending from inside ends of the second inclined portions 770a. Accordingly, it is possible to minimize obstruction of the surgeon's view thanks to the second inclined portions 770a and the second horizontal portion 770b. The shape of the second horizontal portion 770b is an example, and may be formed to be other shapes.

The cut surface seat 790 is accommodated in the second accommodation part 730, and is rotatably mounted to the guide device, and preferably, is mounted to the guide device to be rotatable in a horizontal direction so as to be settled on the first cut surface 820 of proximal tibia 810 of the tibia 800, which is formed to be perpendicular to the mechanical axis M, and thereby it is possible to identify the degree of external rotation of the femur 830 by the guide device 1 during surgery, and the gap G is formed to be an appropriate rectangular space R. The cut surface seat 790 is locked to the second accommodation part 730 to rotate in an inner direction (see FIGS. 11A, 11B, and 11C), and on the contrary, the cut surface seat may be locked to rotate in an outer direction, but not limited thereto. The cut surface seat 790 may include an accommodation hole formed therethrough, and preferably, the accommodation hole is formed through in a vertical direction to accommodate each of the vertical posts 310 therein such that the cut surface seat 790 is securely locked to the second accommodation part 730.

Figure 13:
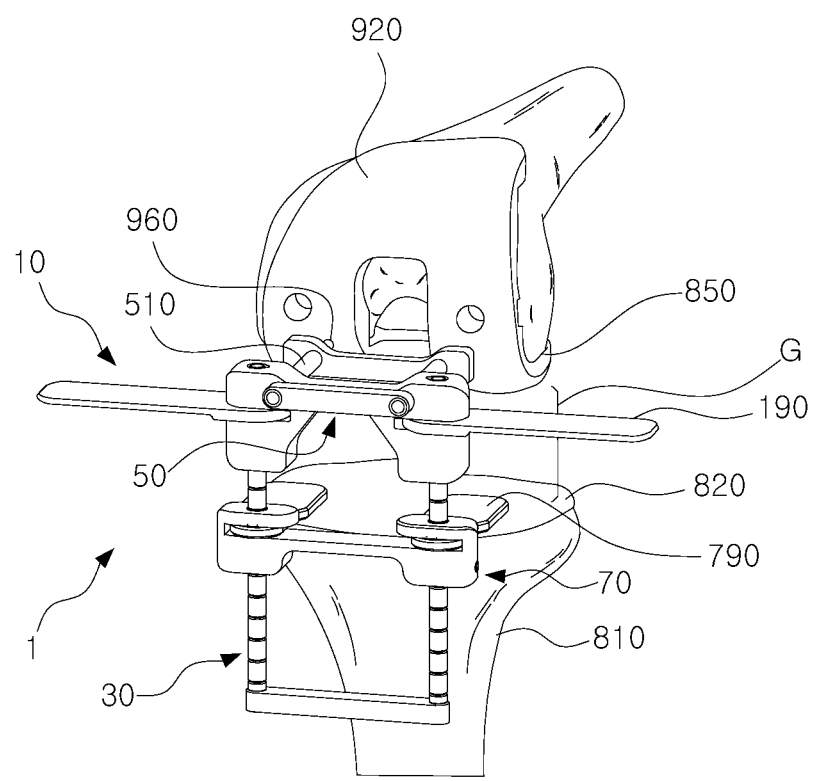
FIG. 13 is a reference view illustrating use of a guide device for knee replacement according to the embodiment of the present invention by being coupled to an implant (or an implant trial)
Figure 14A:
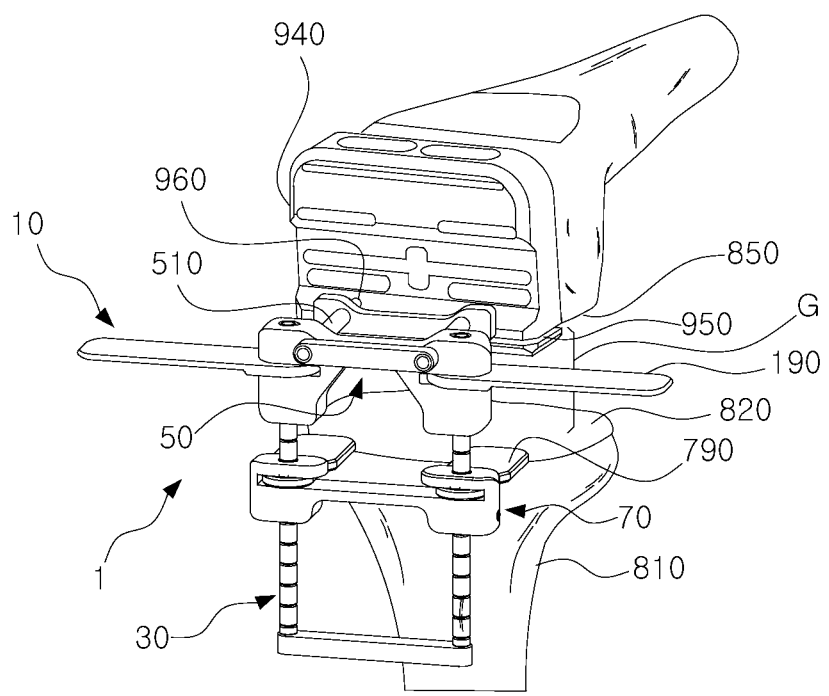
FIGS. 14A and 14B are reference views illustrating use of a guide device for knee replacement according to the embodiment of the present invention by being coupled to the cutting guide.
Figure 14B:
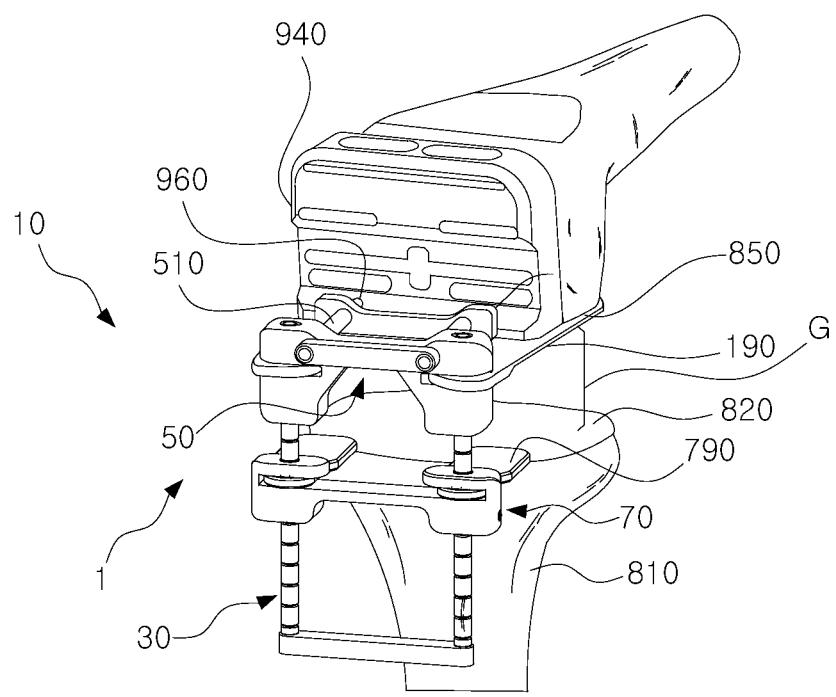

FIG. 13 is a reference view illustrating use of the guide device for knee replacement according to the embodiment of the present invention by being coupled to an implant (or an implant trial); and FIGS. 14A and 14B are reference views illustrating use of the guide device for knee replacement according to the embodiment of the present invention by being coupled to the cutting guide.

Reference will be made to embodiments of use of the guide device 1 during knee replacement surgery and/or knee replacement revision surgery, with reference to FIG. 13, hereinbelow. Firstly, ends of the horizontal posts 510 are inserted into and locked to the slide accommodation part 960 of the cutting guide 940 locked to the proximal tibia 810 by sliding the back-and-forth sliding member 50 in a forward direction. After that, by sliding the up-and-down sliding member 70 in upward and downward directions, the cut surface seat 790 is settled on the first cut surface 820. Thereby, it is possible to determine the height of the implant 900 to be implanted by checking the gap G. Further, referring to FIG. 14, in the case of identifying the degree of external rotation of the femur 830, the external rotation sizing part 190 is inserted into the sizing part accommodation part 950 of the cutting guide 940 from the outside, and thereby it is possible to identify and/or align the degree of external rotation of the femur.

Although a preferred embodiment of the present invention has been described for illustrative purposes, those skilled in the art will appreciate that various modifications, additions and substitutions are possible, without departing from the scope and spirit of the invention as disclosed in the accompanying claims.

DESCRIPTION OF REFERENCE CHARACTERS OF IMPORTANT PARTS

1: guide device for knee replacement
10: upper body
110: first upper limit surfaces
130: first depression part
130a: first inclined portion
130b: first horizontal portion
150: first accommodation part
170: first through-holes
190: external rotation sizing part
30: main body
310: vertical posts
310': annular grooves
330: first lower limit surface
50: back-and-forth sliding member
510: horizontal posts
530: forward sliding limit member
550: backward sliding limit member
70: up-and-down sliding member
70': coupling means accommodation hole
710: second upper limit surfaces
710a: contact part
710b: vertical part
710c: first post accommodation hole
730: second accommodation part
750: second lower limit surfaces
770: second depression part
770a: second inclined portions
770b: second horizontal portion
790: cut surface seat 800: tibia
810: proximal tibia 820: first cut surface
830: femur 840: distal femur
850: second cut surface 900: implant
910: tibial component 920: femoral component
930: bearing 940: cutting guide
950: sizing part accommodation part
960: slide accommodation part
T: transepicondylar axis P: posterior condylar axis
M: mechanical axis G: gap
R: rectangular space

What is claimed is:

1. A guide device for identifying the transepicondylar axis of a knee during knee replacement surgery and revision, the guide device comprising:
   a main body;
   a first sliding member having a surface seat, the surface seat being rotatably secured to the main body so that the surface seat rotates in a first plane perpendicular to a longitudinal axis of a tibia when the guide device is in use; and
   an upper body locked to an upper portion of the main body, the upper body comprising:
      an external sizing part extending perpendicular to the longitudinal axis of the tibia when the guide device is in use, the external sizing part being rotatably secured to the main body so that the external sizing part rotates in a second plane disposed parallel and proximal to the first plane;
   wherein the second plane indicates the transepicondylar axis of a knee when the guide device is in use; and
   wherein the first sliding member is slidable along the main body relative to the upper body so that a gap distance between the surface seat and the external sizing part can be selectively adjusted.

2. The guide device of claim 1, the upper body further comprising:
   a second sliding member configured to slide back-and-forth parallel to the second plane so that the second sliding member may be insertedly and removably coupled to at least one of a cutting guide and an implant during use of the guide device such that the at least one of the cutting guide and the implant is appropriately positioned.

3. The guide device of claim 2, the first sliding member comprising:
   two surface seats extending perpendicular to the longitudinal axis of the tibia when the guide device is in use, the surface seats being rotatably secured to the main body so that the surface seats rotate in the first plane when the guide device is in use.

4. The guide device of claim 2, wherein
   the upper body further includes: first through-holes formed through opposite sides of a front surface of the upper body from the front to the rear, and
   the second sliding member further includes: horizontal posts horizontally provided to be in a cylindrical shape, and accommodated in the first through-holes so as to allow the second sliding member to slide forward and backward; and a forward sliding limit member allowing front ends of the horizontal posts adjacent to each other to be connected to each other, such that when the second sliding member slides forward over a predetermined distance, the forward sliding limit member comes into contact with the front surface of the upper body, thereby preventing the second sliding member from further sliding forward.

5. The guide device of claim 4, wherein the forward sliding limit member is configured such that when the forward sliding limit member comes into contact with the upper body, a predetermined portion of an uppermost portion of the forward sliding limit member protrudes upward higher than an uppermost portion of the upper body, thereby allowing a surgeon to easily grip the second sliding member during use of the guide device.

6. The guide device of claim 4, wherein the second sliding member further includes: a backward sliding limit member allowing rear ends of the horizontal posts adjacent to each other to be connected to each other such that when the second sliding member slides backward over a predetermined distance, the backward sliding limit member comes into contact with a rear surface of the upper body, thereby preventing the second sliding member from further sliding backward.

7. The guide device of claim 6, wherein the backward sliding limit member is provided at a location spaced apart from the rear ends of the horizontal posts by a predetermined distance such that the horizontal posts are inserted into at least one of the cutting guide and a slide accommodation part of the implant during use of the guide device.

8. The guide device of claim 1, the upper body comprising two external sizing parts extending perpendicular to the longitudinal axis of the tibia when the guide device is in use, the external sizing parts being rotatably secured to the main body so that the external sizing parts rotate in the second plane.

9. The guide device of claim 1, wherein the external sizing part rotates in an outer direction when rotating so as not to interfere with a cutting guide when the guide device is in use.

10. The guide device of claim 1, wherein the main body comprises:
  vertical posts being in a cylindrical shape and having a predetermined length in a vertical direction; and
  a first lower limit surface extending such that the vertical posts adjacent to each other are connected to each other, and wherein the first sliding member further comprises:
  second lower limit surfaces being in a predetermined shape at opposite sides of a lower portion of the first sliding member, such that when the first sliding member slides down over a predetermined distance during use, the first lower limit surface and the second lower limit surfaces come into contact with each other to prevent the first sliding member from further sliding down.

11. The guide device of claim 10, wherein outer surfaces of the vertical posts comprise a plurality of annular grooves spaced apart from each other at predetermined intervals along a longitudinal direction thereof, thereby allowing the gap distance to be quickly identified by checking a sliding distance of the first-sliding member during use of the guide device.

12. The guide device of claim 10, wherein the first sliding member further includes: a second depression part provided by being upwardly depressed from inside edges of the second lower limit surfaces by a predetermined height, such that a surgeon's view is not obscured during use of the guide device.

13. The guide device of claim 1, wherein:
  the upper body further comprises first upper limit surfaces inwardly provided at opposite sides of a lower surface of the upper body, each of the first upper limit surfaces being a horizontal surface having a predetermined length and width; and
  the first sliding member further comprises second upper limit surfaces inwardly provided at opposite sides of an upper surface of the first sliding member, each of the second upper limit surfaces being a horizontal surface having a predetermined length and width, such that when the first sliding member slides up over a predetermined distance during use, the first upper limit surfaces and the second upper limit surfaces come into contact with each other to prevent the first sliding member from further sliding up.

14. The guide device of claim 13, wherein the second upper limit surfaces are formed in a reversed L shape and oppositely spaced apart from each other so as to prevent the guide device from blocking a surgeon's view when the guide device is in use.

15. The guide device of claim 14, wherein the upper body further includes: a first depression part provided by being upwardly depressed from inside edges of the first upper limit surfaces to a predetermined height, such that a surgeon's view is not obscured during use of the guide device.

16. The guide device of claim 13, wherein the upper body further includes: a first depression part provided by being upwardly depressed from inside edges of the first upper limit surfaces to a predetermined height, such that a surgeon's view is not obscured during use of the guide device.

* * * * *